United States Patent [19]

Blythin

[11] 4,297,355

[45] * Oct. 27, 1981

[54] (1H,3H,5H)-(1)-BENZOPYRANO-(2,3-D)-PYRIMIDINE-4-ONE-2-THIONES AND THEIR USE AS ANTI-ALLERGY AGENTS

[75] Inventor: David J. Blythin, North Caldwell, N.J.

[73] Assignee: Schering Corporation, Kenilworth, N.J.

[ * ] Notice: The portion of the term of this patent subsequent to Jun. 9, 1998, has been disclaimed.

[21] Appl. No.: 94,407

[22] Filed: Nov. 15, 1979

[51] Int. Cl.$^3$ ................. A61K 31/505; C07D 491/052
[52] U.S. Cl. ................. 424/248.54; 424/251; 544/115; 544/250
[58] Field of Search ................ 544/250, 115; 424/251, 424/248.54

[56] References Cited

U.S. PATENT DOCUMENTS

| | | | |
|---|---|---|---|
| 3,577,420 | 5/1971 | Hess et al. | 544/250 |
| 3,896,128 | 7/1975 | Kast et al. | 544/230 |
| 3,978,059 | 8/1976 | Hardtmann | 544/250 |
| 4,013,646 | 3/1977 | Hardtmann | 424/251 X |
| 4,052,398 | 10/1977 | Kast et al. | 544/230 |
| 4,128,648 | 12/1978 | Rovnyak | 424/251 |
| 4,223,031 | 9/1980 | Covington et al. | 424/251 |

OTHER PUBLICATIONS

Schulte, et al., Arch. Pharm. Ber. Deut. Pharm. Ges. (1972), 305(5), 354–359.
Posner, Organic Reactions, vol. 19, John Wiley & Sons, (1972), pp. 3-4, 78-87.

*Primary Examiner*—Donald G. Daus
*Assistant Examiner*—Diana G. Rivers
*Attorney, Agent, or Firm*—Paul H. Ginsburg

[57] ABSTRACT

This invention relates to (1H,3H,5H)-(1)-benzopyrano-(2,3-d)-pyrimidine-4-one-2-thiones, to pharmaceutically acceptable salts thereof, to the methods for their preparation and to their use as agents in the prophylactic treatment of allergic conditions such as asthma, allergic rhinitis, urticaria and ulcerative colitis.

13 Claims, No Drawings

(1H,3H,5H)-(1)-BENZOPYRANO-(2,3-d)-PYRIMIDINE-4-ONE-2-THIONES AND THEIR USE AS ANTI-ALLERGY AGENTS

DESCRIPTION OF THE INVENTION

This invention relates to certain compositions of matter classified in the art of chemistry as substituted (1H,3H,5H)-(1)-benzopyrano-(2,3-d)-pyrimidine-4-one-2-thiones, the pharmaceutically acceptable salts thereof, to the processes for making such compositions, and to the methods by which they may be utilized as anti-allergy agents in the treatment of such disease states as asthma, allergic rhinitis, urticaria and ulcerative colitis.

This invention, in one of its composition of matter aspects, relates to substituted (1H,3H,5H)-(1)-benzopyrano-(2,3-d)-pyrimidine-4-one-2-thiones, and the pharmaceutically acceptable salts thereof; wherein the substituents are located at the 6-,7-,8-, and/or 9-positions of the benzenoid moiety and wherein the substituents are selected from the group consisting of loweralkyl, lowercycloalkyl, acyloxyloweralkyl, hydroxyloweralkyl, loweralkoxyloweralkyl, nitro, halogeno, hydroxy, lower alkoxy, carboxy, carboxamido, cyano, and loweralkoxycarbonyl.

The invention sought to be patented in another of its composition of matter aspects resides in the concept of a herein defined benzopyranopyrimidine-4-one-2-thione (I) in admixture with a suitable pharmaceutical diluent, carrier or vehicle suitable for enteral or parenteral administration.

The invention sought to be patented in one of its process aspects resides in the concept of administering to a mammal susceptible to and/or suffering from allergic conditions induced by reaginic antibodies, i.e., asthma, urticaria, ulcerative colitis, allergic rhinitis and hay fever, a therapeutically effective quantity of a (1H,3H,5H)-(1)-benzopyrano-(2,3-d)pyrimidine-4-one-2-thione (I), in admixture with a pharmaceutically effective carrier.

More specifically, the tangible embodiments of this invention are those substituted (1H,3H,5H)-(1)-benzopyrano-(2,3-d)-pyrimidine-4-one-2-thiones of the structural formula

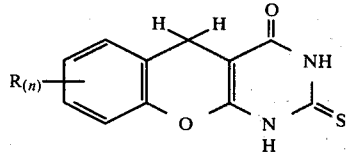

I or the pharmaceutically acceptable salts thereof, wherein R represents loweralkyl, lowercycloalkyl, acyloxyloweralkyl, hydroxyloweralkyl, loweralkoxyloweralkyl, nitro, halogeno, hydroxy, loweralkoxy, alkanoyloxy, carboxy, carboxamido, tetrazolyl, loweralkoxycarbonyl, cyano, and (n) is zero, one or two.

As employed throughout this disclosure, the term "halogeno" refers to fluoro, chloro, bromo and iodo. The term "lower", as it modifies such radicals as alkyl, alkenyl, alkoxy, cycloalkyl, alkylene and the like, defines those radicals having up to six carbon atoms and includes the straight, branched-chain and cyclic manifestations thereof. The term "alkyl" includes methyl, ethyl, propyl, butyl, pentyl and hexyl and isomers thereof, such as isopropyl, t-butyl, neopentyl, dimethylbutyl and the like. "Cycloloweralkyl" includes cyclopropyl, cyclobutyl, cyclopentyl and cyclohexyl. The term "acyloxyloweralkyl" includes those radicals embraced by the partial structure

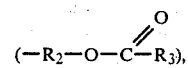

"alkoxyloweralkyl" includes those radicals embraced by the partial structure ($-R_2O-R_1$), and the term "lower alkoxycarbonyl" includes those radicals embraced by the partial structure

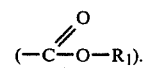

The term "carboxamido" is generic in nature but specifically includes those radicals having the partial structure

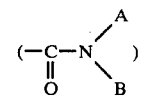

wherein A is straight or branched chain alkyl with up to 12 carbon atoms, lowercycloalkyl, lowercycloalkylloweralkyl, loweralkoxyloweralkyl, hydroxyloweralkyl, fluoroloweralkyl, loweralkenyl, loweralkylthioloweralkyl, loweralkylsulfoxyloweralkyl, loweralkylsulfonylloweralkyl, thiazolyl, oxazolyl, thiadiazolyl, methylthiadiazolyl, furyl, pyrazolyl, tetrazolyl, methyltetrazolyl, phenyl, or the grouping $ER_4$ wherein E is a straight, branched chain or cyclic loweralkylene, optionally substituted with a hydroxy and/or phenyl radical(s), and $R_4$ is phenyl, thiazolyl, oxazolyl, thiadiazolyl, methylthiadiazolyl, tetrazolyl, methyltetrazolyl, furyl, pyridyl, methylpyridyl or piperidinyl; and B is hydrogen, loweralkyl, lowercycloalkyl, lowercycloalkylloweralkyl, or loweralkenyl; or A and B, when taken together with the nitrogen atom to which they are attached, represent imidazolyl, morpholinyl, pyrrolidinyl, piperidinyl or piperazinyl, said heterocyclic rings being optionally substituted by hydroxy, loweralkyl and/or hydroxyloweralkyl.

Where applicable, $R_1$ is loweralkyl, $R_2$ is loweralkylene, and $R_3$ is an alkyl radical having up to 12 carbon atoms including straight and branchedchain manifestations thereof.

When the benzenoid moiety is substituted with radicals such as are defined by R, the most preferred compounds are those wherein "n" is one; it being preferred that the substituent be located at the 7- or the 8- position, although such mono-substituted compounds may have the substituent at any of the 6-, 7-, 8-, or 9-positions. Di-substituted compounds most preferably have at least one substituent at the 7- or the 8-position, and in practice, the di-substituted compounds preferentially bear their substituents at the 7- and 8- positions.

As the compounds are acidic in character they will form physiologically acceptable (i.e., pharmaceutically acceptable) metal or amine cation salts. Illustrative examples of such metals are the alkali metal, i.e., lithium, sodium and potassium, and the alkaline earth metals, i.e., magnesium and calcium. Other metals, i.e., aluminum, zinc and iron are also within the scope of this invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine,α-phenylethylamine, β-phenylethylamine, ethylenediamine, diethylenetriamine and like aliphatic, cycloaliphatic and araliphatic amines containing up to and including about 18 carbon atoms, as well as heterocyclic amines, i.e., piperidine, morpholine, pyrrolidine, piperazine and lower alkyl derivatives thereof, i.e., 1-methyl piperidine, 4-ethylmorpholine, 1-isopropylpyrrolidine, 2-methylpyrrolidine, 1,4-dimethylpiperazine, 2-methylpiperidine, 1,4-dimethylpiperazine, 2-methylpiperidine and the like, as well as amines containing water solubilizing or hydrophilic groups, i.e., mono-, di-, and trietholamine, ethyldiethanolamine, n-butylethanolamine, 2-amino-1-butanol, 2-amino-2-ethyl-1, 3-propanediol, 2-amino-2-methyl-1-propanol, tris (hydroxymethyl) aminomethane, N-phenylethanolamine, N-(p-tetramylphenyl) diethanolamine, galactamine, N-methylglucamine, N-methylglucosamine and the like.

The compounds of this invention may be made by the condensation of an appropriately substituted salicylaldehyde and a 2-thiobarbituric acid in the presence of a sulfonic acid and an alcohol. The condensation reaction is affected by heating the reactants together, preferably at reflux temperatures for times of from ½ to 10 hours. The alcohol is preferably n-propanol or n-butanol although other alcohols having a boiling point of about 100°–140° C. may be utilized. Preferably p-toluene sulfonic acid or methane sulfonic acid is utilized although other sulfonic acids may be used. In practice it is preferred to use 1 to 1 molar equivalents of salicylaldehyde to 2-thiobarbituric acid.

Although the condensation proceeds smoothly to the desired (1H,3H,5H)-(1)-benzypyrano-(2,3-d)-pyrimidine-4-one-2-thiones, the following reaction scheme depicts the mechanisms by which the reaction proceeds.

Of course it is quite obvious to one of ordinary skill in the art that it sometimes is preferred to effect the preparation of a final compound of formula I through a multi-step procedure rather than a single step process. For example, while it is possible to prepare a compound of formula I wherein "R" is a carboxamido moiety by directly condensing a 2-thiobarbituric acid with a carboxamido-containing salicylaldehyde, it is preferred to condense the 2-thiobarbituric acid with a carboxy containing salicylaldehyde and then amidate the carboxyl group to form the carboxamide. Similarly, depending upon the availability of the starting materials, production of undesired side-products and other factors obvious to those of ordinary skill in the art, the following facultative finishing steps may be employed on a condensation "intermediate" to obtain a desired end-product of this invention:

(i) esterification of the carboxyl group representing substituent R;
(ii) de-esterification of a loweralkoxycarbonyl group representing substituent R;
(iii) trans-esterification of a loweralkoxycarbonyl group representing substituent R;
(iv) acylation of any hydroxy group in/or representing substituent R;
(v) de-acylation of acyloxyloweralkyl, alkanoyloxy or acylaminoloweralkyl;
(vi) etherification of any hydroxyl group;
(vii) hydrolysing, alcoholysing or reducing a cyano group;
(viii) oxidation of a hydroxymethyl group;
(ix) acylation of an amino group in substituent
(x) amidation of the carboxyl group to obtain the carboxamido moiety;
(xi) trans-amidation of a carboxamido moiety;
(xii) preparing a pharmaceutically acceptable salt of any of the compounds so obtained. The foregoing facultative finishing steps may be effected by techniques well known in the art.

The foregoing procedures for preparing the compounds of this invention are further illustrated by the examples described below.

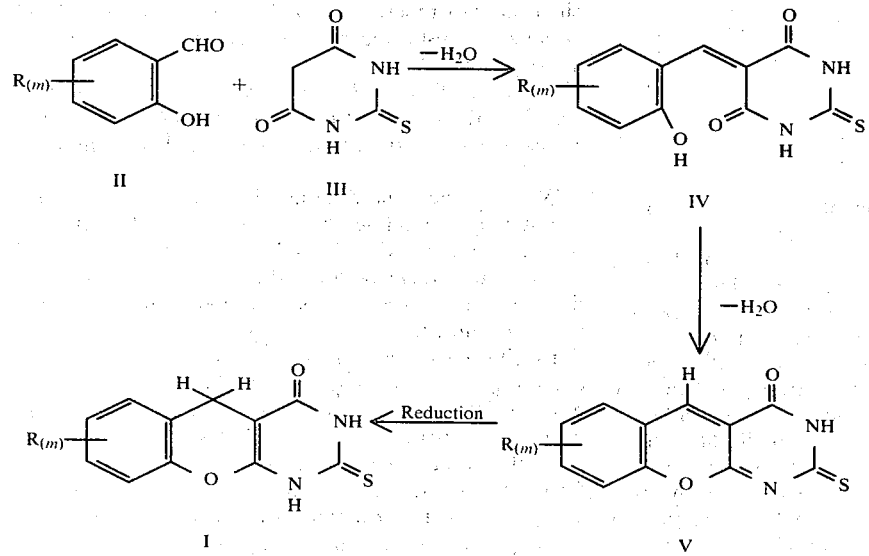

wherein R and (n) are previously described.

EXAMPLE I

7-CYANO-(1H,3H,5H)-(1)-BENZOPYRANO-(2,3-d)-PYRIMIDINE-4-ONE-2-THIONE

To n-butanol (100 ml.) add 5-cyano-salicylaldehyde (6 g.), 2-thiobarbituric acid (6 g.) and methanesulfonic acid (10 ml.) With stirring, heat the mixture to reflux for 1½ hours. Cool, filter, and wash the solid with isopropanol and ether to yield 7-cyano-(1H,3H,5H)-(1)-benzopyrano-(2,3-d)-pyrimidine-4-one-2-thione.

Similarly, by substituting the 5-cyano-salicylaldehyde of this example with the appropriately R-substituted salicylaldehyde and by following the foregoing procedure, there are produced:
7-nitro-(1H,3H,5H)-(1)-benzopyrano-(2,3-d)-pyrimidine-4-one-2-thione,
7-chloro (1H,3H,5H)-(1)-benzopyrano-(2,3-d)-pyrimidine-4-one-2-thione,
7-bromo-(1H,3H,5H)-(1)-benzopyrano-(2,3-d)-pyrimidine-4-one-2-thione,
7-methoxycarbonyl-(1H,3H,5H)-(1)-benzopyrano-(2,3-d)-pyrimidine-4-one-2-thione,
8-ethoxy carbonyl-(1H,3H,5H)-(1)-benzopyrano-(2,3-d)-pyrimidine-4-one-2-thione,
7-nitro-8-trifluoromethyl-(1H,3H,5H)-(1)-benzopyrano-(2,3-d)-pyrimidine-4-one-2-thione,
7-cyano-8-chloro-(1H,3H,5H)-(1)-benzopyrano-(2,3-d)-pyrimidine-4-one-2-thione,
9-methoxy-(1H,3H,5H)-(1)-benzopyrano-(2,3-d)-pyrimidine-4-one-2-thione,
7-tetrazolyl-(1H,3H,5H)-(1)-benzopyrano-(2,3-d)-pyrimidine-4-one-2-thione.
7-methoxy-(1H,3H,5H)-(1)-benzopyrano-(2,3-d)-pyrimidine-4-one-2-thione,
7-methyl-(1H,3H,5H)-(1)-benzopyrano-2,3-d)-pyrimidine-4-one-2-thione,
7,8-dimethyl-(1H,3H,5H)-(1)-benzopyrano-(2,3-d)-pyrimidine-4-one-2-thione,
(1H,3H,5H)-(1)-benzopyrano-(2,3-d)-pyrimidine-4-one-2-thione.

EXAMPLE II

7-CARBOXY-(1H,3H,5H)-(1)-BENZOPYRANO-(2,3-d)-PYRIMIDINE-4-ONE-2-THIONE

Warm a suspension of 7-methoxycarbonyl-(1H,3H,5H)-(1)-benzopyrano-(2,3-d)-pyrimidine-4-one-2-thione (5 g.) in 1 N-sodium hydroxide (25 ml.) until a clear solution is formed and continue the warming for an additional ½ hour. Filter the solution and acidify the filtrate with 2 N sulfuric acid. Filter and wash the solids with water, isopropanol and then ether. Dry the washed solid to obtain. 7-carboxy-2,4-(1H,3H,5H)-(1)-benzopyrano-(2,3-d)-pyrimidine-4-one-2-thione.

In a similar manner, by the use of the appropriately substituted starting material and by following substantially the process of this example there is produced:
6-carboxy-(1H,3H,5H)-(1)-benzopyrano-(2,3-d)-pyrimidine-4-one-2-thione,
8-carboxy-(1H,3H,5H)-(1)-benzopyrano-(2,3-d)-pyrimidine-4-one-2-thione,
9-carboxy-(1H,3H,5H)-(1)-benzopyrano-(2,3-d)-pyrimidine-4-one-2-thione, 7,8-dicarboxy-(1H,3H,5H)-(1)-benzopyrano-(2,3-d)-pyrimidine-4-one-2-thione.

EXAMPLE III

7-(IMIDAZOLYLCARBONYL)-(1H,3H,5H)-(1)-BENZOPYRANO-(2,3-d)-PYRIMIDINE-4-ONE-2-THIONE

Add N,N'-carbonyldiimidazole (70 g.) in portions to a suspension of 7-carboxy-(1H,3H,5H)-(1)-benzopyrano-(2,3-d)-pyrimidine-4-one-2-thione (30 g.) in dry dimethylformamide (300 ml.). Heat to 70° C. for 3 hours. Cool, filter, wash with ether and dry to give 7-(imidazolylcarbonyl)-(1H,3H,5H)-(1)-benzopyrano-(2,3-d)-pyrimidine-4-one-2-thione.

In a similar manner, by the use of the appropriately carboxyl-substituted compounds (as prepared by the teachings of Example II), and by following substantially the process of this example there is produced the corresponding imidazolylcarbonylsubstituted (or disubstituted) (1H,3H,5H)-(1)-benzopyrano-(2,3-d)-pyrimidine-4-one-2-thione.

EXAMPLE IV

7-(5-TETRAZOLYLAMINOCARBONYL)-(1H,3H,5H)-(1)-BENZOPYRANO-(2,3-d)-PYRIMIDINE-4-ONE-2-THIONE

Suspend 7-(imidazolylcarbonyl)-(1H,3H,5H)-(1)-benzopyrano-(2,3-d)-pyrimidine-4-one-2-thione (0.6 g.) in dry dimethylformamide (20 ml.). With stirring, add 5-aminotetrazole (0.61 g.) and warm the mixture to 65°–75° C. and keep at that temperature for about ¾ hour. Allow the mixture to cool, pour into water and acidify with hydrochloric acid. Filter and wash with isopropanol and ether to yield 7-(5-tetrazolylaminocarbonyl)-(1H,3H,5H)-(1)-benzopyrano-(2,3-d)-pyrimidine-4-one-2-thione.

Prepared in essentially the same way except that if a basic ring is present, e.g., pyridine, the basic reaction product is either neutralized with acid, or acidified with HCl and the product isolated as the hydrochloride salt:
7-aminocarbonyl-(1H,3H,5H)-(1)-benzopyrano-(2,3-d)-pyrimidine-4-one-2-thione,
7-methylaminocarbonyl-(1H,3H,5H)-(1)-benzopyrano-(2,3-d)-pyrimidine-4-one-2-thione,
7-ethylaminocarbonyl-(1H,3H,5H)-(1)-benzopyrano-(2,3-d)-pyrimidine-4-one-2-thione,
7-n-propylaminocarbonyl-(1H,3H,5H)-(1)-benzopyrano-(2,3-d)-pyrimidine-4-one-2-thione,
7-iso-propylaminocarbonyl-(1H,3H,5H)-(1)-benzopyrano-(2,3-d)-pyrimidine-4-one-2-thione,
7-n-butylaminocarbonyl-(1H,3H,5H)-(1)-benzopyrano-(2,3-d)-pyrimidine-4-one-2-thione,
7-iso-butylaminocarbonyl-(1H,3H,5H)-(1)-benzopyrano-(2,3-d)-pyrimidine-4-one-2-thione,
7-sec-butylaminocarbonyl-(1H,3H,5H)-(1)-benzopyrano-(2,3-d)-pyrimidine-4-one-2-thione,
7-tert-butylaminocarbonyl-(1H,3H,5H)-(1)-benzopyrano-(2,3-d)-pyrimidine-4-one-2-thione,
7-n-pentylaminocarbonyl-(1H,3H,5H)-(1)-benzopyrano-(2,3-d)-pyrimidine-4-one-2-thione,
7-n-hexylaminocarbonyl-(1H,3H,5H)-(1)-benzopyrano-(2,3-d)-pyrimidine-4-one-2-thione,
7-n-octylaminocarbonyl-(1H,3H,5H)-(1)-benzopyrano-(2,3-d)-pyrimidine-4-one-2-thione,
7-n-decylaminocarbonyl-(1H,3H,5H)-(1)-benzopyrano-(2,3-d)-pyrimidine-4-one-2-thione,
7-benzylaminocarbonyl-(1H,3H,5H)-(1)-benzopyrano-(2,3-d)-pyrimidine-4-one-2-thione, 7-cyclopropylaminocarbonyl-(1H,3H,5H)-(1)-benzopyrano-(2,3-d)-pyrimidine-4-one-2-thione,
7-cyclobutylaminocarbonyl-(1H,3H,5H)-(1)-benzopyrano-(2,3-d)-pyrimidine-4-one-2-thione,
7-cyclopentylaminocarbonyl-(1H,3H,5H)-(1)-benzopyrano-(2,3-d)-pyrimidine-4-one-2-thione,
7-cyclohexylaminocarbonyl-(1H,3H,5H)-(1)-benzopyrano-(2,3-d)-pyrimidine-4-one-2-thione,
7-cycloheptylaminocarbonyl-(1H,3H,5H)-(1)-benzopyrano-(2,3-d)-pyrimidine-4-one-2-thione,
7-cyclopropylmethylaminocarbonyl-(1H,3H,5H)-(1)-benzopyrano-(2,3-d)-pyrimidine-4-one-2-thione,
7-cyclobutylmethylaminocarbonyl-(1H,3H,5H)-(1)-benzopyrano-(2,3-d)-pyrimidine-4-one-2-thione,
8-methylaminocarbonyl-(1H,3H,5H)-(1)-benzopyrano-(2,3-d)-pyrimidine-4-one-2-thione,
8-ethylaminocarbonyl-(1H,3H,5H)-(1)-benzopyrano-(2,3-d)-pyrimidine-4-one-2-thione,
8-n-propylaminocarbonyl-(1H,3H,5H)-(1)-benzopyrano-(2,3-d)-pyrimidine-4-one-2-thione,
8-iso-propylaminocarbonyl-(1H,3H,5H)-(1)-benzopyrano-(2,3-d)-pyrimidine-4-one-2-thione,
8-n-butylaminocarbonyl-(1H,3H,5H)-(1)-benzopyrano-(2,3-d)-pyrimidine-4-one-2-thione,
8-iso-butylaminocarbonyl-(1H,3H,5H)-(1)-benzopyrano-(2,3-d)-pyrimidine-4-one-2-thione,
8-n-pentylaminocarbonyl-(1H,3H,5H)-(1)-benzopyrano-(2,3-d)-pyrimidine-4-one-2-thione,
7-(2-[2-pyridyl]ethylaminocarbonyl)-(1H,3H,5H)-(1)-benzopyrano-(2,3-d)-pyrimidine-4-one-2-thione,
7-(2-[3-pyridyl]ethylaminocarbonyl)-(1H,3H,5H)-(1)-benzopyrano-(2,3-d)-pyrimidine-4-one-2-thione,
7-(2-[4-pyridyl]ethylaminocarbonyl)-(1H,3H,5H)-(1)-benzopyrano-(2,3-d)-pyrimidine-4-one-2-thione,
7-(2-pyridylmethylaminocarbonyl)-(1H,3H,5H)-(1)-benzopyrano-(2,3-d)-pyrimidine-4-one-2-thione,
7-(3-pyridylmethylaminocarbonyl)-(1H,3H,5H)-(1)-benzopyrano-(2,3-d)-pyrimidine-4-one-2-thione,
7-(4-pyridylmethylaminocarbonyl)-(1H,3H,5H)-(1)-benzopyrano-(2,3-d)-pyrimidine-4-one-2-thione,
7-(3-[2-pyridyl]propylaminocarbonyl)-(1H,3H,5H)-(1)-benzopyrano-(2,3-d)-pyrimidine-4-one-2-thione,
7-(3-[3-pyridyl]propylaminocarbonyl)-(1H,3H,5H)-(1)-benzopyrano-(2,3-d)-pyrimidine-4-one-2-thione,
7-(3-[4-pyridyl]propylaminocarbonyl)-(1H,3H,5H)-(1)-benzopyrano-(2,3-d)-pyrimidine-4-one-2-thione,
7-(2-[6'-methyl-2'-pyridyl]ethylaminocarbonyl)-(1H,3H,5H)-(1)-benzopyrano-(2,3-d)-pyrimidine-4-one-2-thione,
8-(2-[2-pyridyl]ethylaminocarbonyl)-(1H,3H,5H)-(1)-benzopyrano-(2,3-d)-pyrimidine-4-one-2-thione,
8-(2-[3-pyridyl]ethylaminocarbonyl)-(1H,3H,5H)-(1)-benzopyrano-(2,3-d)-pyrimidine-4-one-2-thione,
8-(2-[4-pyridyl]ethylaminocarbonyl)-(1H,3H,5H)-(1)-benzopyrano-(2,3-d)-pyrimidine-4-one-2-thione,
8-(2-pyridylmethylaminocarbonyl)-(1H,3H,5H)-(1)-benzopyrano-(2,3-d)-pyrimidine-4-one-2-thione,
8-(3-[2-pyridyl]propylaminocarbonyl)-(1H,3H,5H)-(1)-benzopyrano-(2,3-d)-pyrimidine-4-one-2-thione,
8-(2-[6'-methyl-2'-pyridyl]ethylaminocarbonyl)-(1H,3H,5H)-(1)-benzopyrano-(2,3-d)-pyrimidine-4-one-2-thione,
7-(2-hydroxy-2-phenyl)-ethylaminocarbonyl)-(1H,3H,5H)-(1)-benzopyrano-(2,3-d)-pyrimidine-4-one-2-thione,
8-(2-hydroxy-2-phenyl)-ethylaminocarbonyl)-(1H,3H,5H)-(1)-benzopyrano-(2,3-d)-pyrimidine-4-one-2-thione,
7-methoxyethylaminocarbonyl-(1H,3H,5H)-(1)-benzopyrano-(2,3-d)-pyrimidine-4-one-2-thione,
7-hydroxyethylaminocarbonyl-(1H,3H,5H)-(1)-benzopyrano-(2,3-d)-pyrimidine-4-one-2-thione,
7-(3'-hydroxypropylaminocarbonyl)-(1H,3H,5H)-(1)-benzopyrano-(2,3-d)-pyrimidine-4-one-2-thione,
7-dimethylaminocarbonyl-(1H,3H,5H)-(1)-benzopyrano-(2,3-d)-pyrimidine-4-one-2-thione,
7-diethylaminocarbonyl-(1H,3H,5H)-(1)-benzopyrano-(2,3-d)-pyrimidine-4-one-2-thione,
7-morpholinocarbonyl-(1H,3H,5H)-(1)-benzopyrano-(2,3-d)-pyrimidine-4-one-2-thione,
7-pyrrolidinocarbonyl-(1H,3H,5H)-(1)-benzopyrano-(2,3-d)-pyrimidine-4-one-2-thione,
7-piperidinocarbonyl-(1H,3H,5H)-(1)-benzopyrano-(2,3-d)-pyrimidine-4-one-2-thione,
7-(N'-methylpiperazinyl)-(1H,3H,5H)-(1)-benzopyrano-(2,3-d)-pyrimidine-4-one-2-thione,
7-(N'-hydroxyethylpiperazinylcarbonyl)-(1H,3H,5H)-(1)-benzopyrano-(2,3-d)-pyrimidine-4-one-2-thione,
8-methoxyethylaminocarbonyl-(1H,3H,5H)-(1)-benzopyrano-(2,3-d)-pyrimidine-4-one-2-thione,
8-hydroxyethylaminocarbonyl-(1H,3H,5H)-(1)-benzopyrano-(2,3-d)-pyrimidine-4-one-2-thione,
8-diethylaminocarbonyl-(1H,3H,5H)-(1)-benzopyrano-(2,3-d)-pyrimidine-4-one-2-thione,
8-morpholinocarbonyl-(1H,3H,5H)-(1)-benzopyrano-(2,3-d)-pyrimidine-4-one-2-thione,
7-(2-thiazolylaminocarbonyl)-(1H,3H,5H)-(1)-benzopyrano-(2,3-d)-pyrimidine-4-one-2-thione,
7-(2-oxazolylaminocarbonyl)-(1H,3H,5H)-(1)-benzopyrano-(2,3-d)-pyrimidine-4-one-2-thione,
7-(3-pyrazolylaminocarbonyl)-(1H,3H,5H)-(1)-benzopyrano-(2,3-d)-pyrimidine-4-one-2-thione,
7-(2-methyl-5-tetrazolylaminocarbonyl)-(1H,3H,5H)-(1)-benzopyrano-(2,3-d)-pyrimidine-4-one-2-thione.

EXAMPLE V

7-(n-BUTYLAMINOCARBONYL)-(1H,3H,5H)-(1)-BENZOPYRANO(2,3-d)-PYRIMIDINE-4-ONE-2-THIONE 7-(Imidazolylcarbonyl)-(1H,3H,5H)-(1)-benzopyrano-(2,3-d)-pyrimidine-4-one-2-thione (1 g.) is suspended in dry dimethylformamide (60 ml.) and n-butylamine (1.1 g.) is added. The mixture is stirred at room temperature overnight then at 70° C. for 1½ hours. The product is added to dilute HCl and the solid is collected, washed with water, ethanol and ether and dried to yield the desired 7-(n-butylaminocarbonyl)-(1H,3H,5H)-(1)-benzopyrano-(2,3-d)-pyrimidine-4-one-2-thione.

EXAMPLE VI

7-(5-TETRAZOLYLAMINOCARBONYL)-(1H,3H,5H)-(1)-BENZOPYRANO(2,3-d)-PYRIMIDINE-4-ONE-2-THIONE

To a suspension of 7-carboxyl-(1H,3H,5H)-(1)-benzopyrano-(2,3-d)-pyrimidine-4-one-2-thione (2.46 g.) in dry dimethylformamide (160 ml.) at 75° C., add (all at once), N,N'-carbonyldiimidazole (3.05 g.). Heat the resulting mixture at 68°–73° C. for 20 minutes, then add a solution of 5-aminotetrazole (0.80 g.) in dry dimethylformamide (11 ml.) at 40° C. Stir the resulting mixture overnight at room temperature and heat at 50° C. for 24 hours. Chill the resulting mixture at 0° C. for one day, filter, triturate with ether (25 ml.), triturate with 20% v/v ethanol/ether, filter, wash with ether and vacuum dry at 54° C. for two hours, to yield 7-(5-tetrazolylaminocarbonyl)-(1H,3H,5H)-(1)-benzopyrano-(2,3-d)-pyrimidine-4-one-2-thione.

Also, by the teachings of this and of Example V, the compounds listed under Example IV may also be produced.

EXAMPLE VII

7-(n-PROPYLOXYCARBONYL)-(1H,3H,5H)-(1)-BENZOPYRANO(2,3-d)-PYRIMIDINE-4-ONE-2-THIONE

To a solution of 5-carboxysalicyaldehyde (6.5 g.) and 2-thiobarbituric acid (6 g.) in n-propanol (100 ml.), add methanesulfonic acid (10 ml.). Warm the solution gradually, with stirring, to reflux during about 2 hours, then for 1½ hours. Cool, filter and wash the solid with cold ethanol and ether to yield 7-(n-propyloxycarbonyl)-(1H,3H,5H)-(1)-benzopyrano-(2,3-d)-pyrimidine-4-one-2-thione.

Similarly, by substituting the n-propanol of this example with other primary alcohols and heating at 100°–140° C. for ½–6 hours under pressure, if necessary, there are produced:

7-(n-butyloxycarbonyl)-(1H,3H,5H)-(1)-benzopyrano-(2,3-d)-pyrimidine-4-one-2-thione,
7-(n-pentyloxycarbonyl)-(1H,3H,5H)-(1)-benzopyrano-(2,3-d)-pyrimidine-4-one-2-thione,
7-(2'-methylbutyloxycarbonyl)-(1H,3H,5H)-(1)-benzopyrano-(2,3-d)-pyrimidine-4-one-2-thione,
7-cyclopentylmethyloxycarbonyl)-(1H,3H,5H)-(1)-benzopyrano-(2,3-d)-pyrimidine-4-one-2-thione.
7-(isopropyloxycarbonyl)-(1H,3H,5H)-(1)-benzopyrano-(2,3-d)-pyrimidine-4-one-2-thione.
7-(isobutyloxycarbonyl)-(1H,3H,5H)-(1)-benzopyrano-(2,3-d)-pyrimidine-4-one-2-thione.

EXAMPLE VIII

7-n-BUTYLOXYMETHYL-(1H,3H,5H)-(1)-BENZOPYRANO-(2,3-d)PYRIMIDINE-4-ONE-2-THIONE

To a solution of 5-hydroxymethyl-salicylaldehyde (5.8 g.) and 2-thiobarbituric acid (6 g.) in n-butanol (100 ml.) add methanesulfonic acid (10 ml.) and heat to reflux, with stirring, for 1 hour. Cool, filter and wash the solid with ethanol and ether to yield 7-n-butyloxymethyl-(1H,3H,5H)-(1)-benzopyrano-(2,3-d)-pyrimidine-4-one-2-thione.

Similarly, by substituting the 5-hydroxymethyl-salicylaldehyde of this example with the appropriately R-substituted salicylaldehyde and the n-butanol with another primary or secondary alcohol having a boiling point of at least 100° C. and heating at 100° C.–140° C. there are produced:

7-n-propyloxymethyl-(1H,3H,5H)-(1)-benzopyrano-(2,3-d)-pyrimidine-4-one-2-thione,
7-n-butyloxyethyl-(1H,3H,5H)-(1)-benzopyrano-(2,3-d)-pyrimidine-4-one-2-thione,
7-n-pentyloxymethyl-(1H,3H,5H)-(1)-benzopyrano-(2,3-d)-pyrimidinedione-4-one-2-thione.

EXAMPLE IX

7-HYDROXYMETHYL-(1H,3H,5H)-(1)-BENZOPYRANO(2,3-d)-PYRIMIDINE-4-ONE-2-THIONE

Reflux a solution of 7-(n-butyloxymethyl)-(1H,3H,5H)-(1)-benzopyrano-(2,3-d)-pyrimidine-4-one-thione (5 g.) with 48% HBr (100 ml.) for 4 hours. Cool and filter off the solid. Dissolve the solid in 1N-NaOH (100 ml.) under nitrogen and stir at ambient temperature for 24 hours. Acidify with 5N-HCl, filter, and wash the product with water, ethanol and ether to yield 7-hydroxymethyl-(1H,3H,5H)-(1)-benzopyrano-(2,3-d)-pyrimidine-4-one-2-thione.

Similarly, by following the above procedure there are produced:

7-(2'-hydroxyethyl)-(1H,3H,5H)-(1)-benzopyrano-(2,3-d)-pyrimidine-4-one-2-thione,
8-hydroxymethyl-(1H,3H,5H)-(1)-benzopyrano-(2,3-d)-pyrimidine-4-one-2-thione,
8-(2'-hydroxyethyl)-(1H,3H,5H)-(1)-benzopyrano-(2,3-d)-pyrimidine-4-one-2-thione,
7-(2'-hydroxypropyl)-(1H,3H,5H)-(1)-benzopyrano-(2,3-d)-pyrimidine-4-one-2-thione,
7-hydroxymethyl-9-nitro-(1H,3H,5H)-(1)-benzopyrano-(2,3-d)-pyrimidine-4-one-2-thione,
7-hydroxymethyl-9-chloro-(1H,3H,5H)-(1)-benzopyrano-(2,3-d)-pyrimidine-4-one-2-thione,

EXAMPLE X

7-(ISOBUTYRYLOXYMETHYL)-(1H,3H,5H)-(1)-BENZOPYRANO-(2,3-d)-PYRIMIDINE-4-ONE-2-THIONE

To a cooled (below 5° C.) suspension of 7-hydroxymethyl-(1H,3H,5H)-(1)-benzopyrano-(2,3-d)-pyrimidine-4-one-2-thione (2.8 g.) in dry pyridine (100 ml.), add isobutyric anhydride (20 ml.). Keep the mixture cold for 24 hours and stir the mixture at 20° C. for an additional two days. Pour the mixture over ice water, filter and successively wash the solids with water, ethanol and ether. Dry the washed solids to obtain 7-(isobutyryloxymethyl)-(1H,3H,5H)-(1)-benzopyrano-(2,3-d)-pyrimidine-4-one-2-thione.

Similarly, by starting with other pyrimidine-4-one-2-thiones of this invention which bear one or more reactive hydroxyl groups (i.e., when R represents hydroxyalkyl), the foregoing esterification may be affected. Analogously, by utilizing the acid chloride or anhydride of the appropriate acid and following the techniques of this example, the following esters may be prepared: acetyl, propionyl, n-butyryl, isobutyryl, pivaloyl, t-butylacetyl, cyclopropylcarboxyl, cyclobutylcarboxyl, cyclopentylcarboxyl, 1-adamantylcarboxyl, lauroyl, benzoyl and ethyl oxalyl.

EXAMPLE XI

7-ETHOXYCARBONYL-(1H,3H,5H)-(1)-BENZOPYRANO(2,3-d)-PYRIMIDINE-4-ONE-2-THIONE

Suspend 7-carboxy-(1H,3H,5H)-(1)-benzopyrano-(2,3-d)-pyrimidine-4-one-2-thione (5 g.) in ethanol and pass in HCl gas until saturated. Reflux the mixture for 24 hours then cool, filter and wash with ethanol and ether to yield 7-ethoxycarbonyl(1H,3H,5H)-(1)-benzopyrano-(2,3-d)-pyrimidine-4-one-2-thione.

Similarly can be prepared:

7-(iso-butyloxycarbonyl)-(1H,3H,5H)-(1)-benzopyrano-(2,3-d)-pyrimidine-4-one-2-thione,
7-benzoyloxycarbonyl-(1H,3H,5H)-(1)-benzopyrano-(2,3-d)-pyrimidine-4-one-2-thione.

EXAMPLE XII

ISOLATION OF THE (N-METHYL-D-GLUCAMINE) SALT OF 7-(5'-TETRAZOLYLAMINOCARBONYL)-(1H,3H,5H)-(1)-BENZOPYRANO(2,3-d)-PYRIMIDINE-4-ONE-2-THIONE

Dissolve N-methyl-D-glucamine (11.4 g.) in water (200 ml.). Add 7-(5'-tetrazolylaminocarbonyl)-(1H,3H,5H)-(1)-benzopyrano (2,3-d)-pyrimidine-4-one-2-thione (10 g.) and stir until dissolved. Filter and lyophilize to yield the bis-NMG salt of 7-(5'-tetrazolylaminocarbonyl)-(1H,3H,5H)-(1)-benzopyrano-(2,3-d)-pyrimidine-4-one-2-thione.

Similarly may be prepared the salts of any of the compounds disclosed here with the exception that if the compound is a monobasic acid only one equivalent of N-methyl-D-glucamine is used.

The compounds of the invention (I) have the applied use characteristic of being anti-allergic agents useful in the prophylactic treatment of sensitized animals for allergy and anaphylactic reactions of a reagin or non-reagin mediated nature and as such are useful in the treatment of such disease states as asthma, allergic rhinitis, urticaria and other allergic conditions induced by reaginic antibodies.

In testing the compounds of this invention, the two primary assays utilized are the Passive Cutaneous Anaphylaxis (PCA) assay and the Antigen induced histamine release from rat peritoneal mast cells passively sensitized in vivo assay. The compounds are additionally tested as antagonists of intradermally injected histamine and serotonin; these secondary tests show that the compounds are not working as classical antihistamine or antiserotonin anti-allergy agents.

These tests may be briefly described as follows: Preparation of Antisera Containing Homocytotropic Antibody (IgE) to N. Brasiliensis: Male Sprague-Dawley rats, 150-200 g., were injectd subcutaneously with 3000 larvae and 28 days later were reinfected with 3000 larvae. Serum was collected 7-12 days following reinfection and frozen in small aliquots at −40° C.

Preparation of Antigen: Adult worms were harvested from the small intestine of rats 8-11 days after infection with larvae. A homogenate was prepared from a suspension of worms in 0.15 M saline using a ground glass homogenizer. The homogenate was centrifuged at 3000× g. for 15 minutes in a Sorvall RC2-B centrifuge. The supernatant was carefully removed and frozen at 40° C. Just prior to use as antigen, the supernatant was adjusted to a concentration of 5 mg. protein per milliliter. All antigen preparations were standardized in this way although it is recognized that the protein concentration of this crude worm extract does not necessarily reflect the amount of specific antigen present in the extract.

Passive Cutaneous Anaphylaxis (PCA): Male Sprague-Dawley rats weighing 250-300 g. were used for PCA reactions. Nine two-fold dilutions of antisera containing homocytotropic antibodies against N. brasiliensis were made in 0.15 M saline. Each dilution was injected intradermally at separate sites onto the shaved backs of normal rats and 48 hours later the animals were challenged intravenously with 0.1 ml. antigen (worm extract) mixed with 0.9 ml. of one percent Evans blue dye. The animals were sacrificed 45 minutes following antigen challenge, skinned, and the area of blueing measured with a millimeter rule. The diameter of the sites of reaction were graded as follows:

| Diameter | Score |
| --- | --- |
| 20 (or greater) | 4 |
| 15–19 | 3 |
| 14–10 | 2 |
| 5–9 | 1 |

The intensity of the reaction was also graded from 0–4.

Histamine Release from Rat Peritoneal Mast Cells Passively Sensitized in vivo: The method used in these studies is a modification of that of Orange, et al. Briefly, male Sprague-Dawley rats (CD strain), 150–200 g. were injected i.p. with 2.0 ml. of a dilution of rat antisera containing HA. Two hours later the animals were challenged with 100 mg. worm protein in 5.0 ml. Tyrode's solution containing 50 mg/ml of heparin. Exactly five minutes later, the peritoneal fluid was harvested and centrifuged at 150× g. for five minutes at 4° C. The supernatants were removed, and the cells were resuspended in 1.0 ml. Tyrode's and boiled for seven minutes to extract residual cell histamine. The supernatant and cell extracts were frozen at −70° C. and later assayed for their histamine content.

Histamine Release in vitro from Passively Sensitized Mast Cells: Peritoneal mast cells were obtained from normal animals, pooled, washed and resuspended in Tyrode's minus gelatin buffer. An equal volume of serum containing rat homocytotropic antibody was added to the cell suspension and the mixture was incubated at 37° C. for two hours in a metabolic shaker. The suspension was then centrifuged at 150× g. for 10 minutes and the supernatant discarded. The cells were resuspended in Tyrode's minus gelatin, combined with antigen, and incubated for five minutes at 37° C. The cells were harvested by centrifugation and the supernatants immediately frozen at −70° C. Residual histamine was extracted from the cells by boiling them for seven minutes in 1.0 ml. Tyrode's minus gelatin.

Histamine Release in vitro from Actively Sensitized Mast Cells: Peritoneal mast cells were obtained from rats 21–18 days following infection with 3000 Nippostronglus (NB) larvae. The cells were washed and suspended in Tyrode's buffer. Inhibitor dissolved in Tyrode's was added one minute before antigen. An equal volume of antigen, prewarmed to 37° C., was added and the mixture incubated at 37° C. for 15 minutes. The cells and supernatant were then processed as described above for passive sensitization. Both in vitro methods are essentially those described by Wilson, et al.

Histamine Assay: The fluorescent assay of Shore, et al. as modified by Technicon for automated determination of histamine was employed.

Determination of Antihistamine and Antiserotonin Activities of Compounds: Normal rats, 200–250 g., were injected i.d. with 10, 20 and 50 μg. of histamine and/or serotonin at separate sites on their backs 30 or 60 minutes following i.p. or oral administration of drug, respectively. Immediately following the last i.d. injection, the animals received 1 ml. of a one percent solution of Evans blue dye intraveneously. Fifteen minutes later they were sacrificed, and the area of blueing measured with a millimeter rule. Each compound was tested for antihistamine or antiserotonin activity in nine animals.

From these tests, as well as by comparison with known anti-allergy agents of similar type activity (i.e., Intal), the compounds are found to be effective in the treatment of the above mentioned allergic disease states and such activity is not a function of classical antihistamine or antiserotonin characteristics. The compounds are effective for their end-use at varying dose ranges, depending on the method administration. For example, the more active compounds have an effective intraperitoneal administered dose of 0.1-10 MPK, an effective intravenous administered dose of 0.01-10 MPK, and an effective oral dosage of 25-200 MPK, each given at least once per day but also such doses may be repeated as the attending diagnostician sees fit. In general, the compounds of this invention, when compared with the clinical effectiveness of Intal-like compounds in aerosol or inhalation preparations are effective at 1-20. mg. per day, preferably in divided doses.

In their use as anti-allergy agents, the compounds of this invention are administered in unit dosage forms, such as tablets, capsules, pills, powders, granules, sterile parenteral solutions or suspensions, eye drops, oral solutions or suspensions, and oil-in-water and water-in-oil emulsions containing suitable quantities of the compounds of this invention (I). The preferred method of administration is by inhalation into the lung or nasal passages by means of an aerosol liquid, or powder for insufflation, or orally.

For oral administration, either solid or fluid unit dosage forms can be prepared. For preparing solid compositions such as tablets, the compounds of this invention (I) are mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by machine encapsulation of a slurry of the compound with an acceptable vegetable oil, light liquid petrolatum or other inert oil.

Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. Advantageously, a surfactant or wetting agent is included in the composition to facilitate uniform distribution of the compound.

Additionally, a rectal suppository can be employed to deliver the active compound. This dosage form is of particular interest where the mammal cannot be treated conventionally by means of other dosage forms, such as orally or by insufflation, as in the case of young chldren or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1-2.5 g.

The preferred compositions are those adapted for inhalation into the lung. For treatment of allergic conditions of the nose, such as rhinitis, compositions adapted for contact with nasal linings are preferred.

Compositions for inhalation are of three basic types: (1) a powder mixture preferably micropulverized with particle size, preferably from about 1 to about 5 microns; (2) an aqueous solution or suspension to be sprayed with a nebulizer; and (3) an aerosol with volatile propellant in a pressurized container.

The powders are quite simply prepared by mixing a compound of formula (I) with a solid carrier which is compatible with lung tissue, preferably lactose. The powders are packaged in a device adapted to emit a measured amount of powder when inhaled through the mouth. Aqueous solutions are prepared by dissolving the compounds of this invention as salts in water and buffering to a pH compatible with inhalation. The solutions are dispersed in a spray device or nebulizer and sprayed into the mouth while inhaling. Aerosols are prepared by dispersing a compound of this invention (I) in water or ethanol and placing the dispersion and a volatile propellant in a pressurized container.

Examples of suitable unit dosage forms in accordance with this invention are tablets, capsules, pills, suppositories, powder packets, wafers, granules, cachets, teaspoonfuls, tablespoonfuls, dropperfuls, ampuls, vials, aerosols with meter discharges, segregated multiples of any of the foregoing.

The following are specific examples of effective pharmaceutical formulations by which the compounds of this invention may be administered.

EXAMPLE XII

A lot of 10,000 tablets, each containing 50 mg. of 7-[5′-tetrazolylaminocarbonyl]-(1H,3H,5H)-(1)-benzopyrano-(2,3-d)-pyrimidine-4-one-2-thione is prepared from the following types and amounts of ingredients:

| | |
|---|---|
| 7-[5′tetrazolylaminocarbonyl]-(1H,3H,5H)-(1)-benzopyrano-(2,3-d)-pyrimidine-4-one-2-thione | 500 gm. |
| Dicalcium phosphate | 1000 gm. |
| Methylcellulose U.S.P. (15 cps.) | 60 gm. |
| Talc | 150 gm. |
| Corn starch | 200 gm. |
| Magnesium stearate | 10 gm. |

The compound and dicalcium phosphate are mixed well, granulated with 7.5 percent solution of methylcellulose in water, passed through a No. 8 screen and dried carefully. The dried granules are passed through a No.

12 screen, mixed thoroughly with the talc, starch and magnesium stearate, and compressed into tablets.

These tablets are useful in preventing hay fever or asthma attacks at a dose of one tablet every 6 hours.

EXAMPLE XIII

One thousand tablets, each containing 50 mg. of 7-[5′-tetrazolylaminocarbonyl]-(1H,3H,5H)-(1)-benzopyrano-(2,3-d)-pyrimidine-4-one-2-thione are prepared from the following types and amounts of ingredients:

| | |
|---|---|
| 7-[5′-tetrazolylaminocarbonyl]-(1H,3H,5H)-(1)-benzopyrano-(2,3-d)-pyrimidine-4-one-2-thione | 50 gm. |
| Microcrystalline cellulose, NF | 410 gm. |
| Starch | 100 gm. |
| Magnesium stearate powder | 3 gm. |

The ingredients are screened and blended together and presses into tablets.

The tablets are useful to protect against food-allergy at a dose of one tablet before meals.

EXAMPLE XIV

A sterile preparation suitable for intramuscular injection and containing 5 mg. of 7-[5′-tetrazolylaminocarbonyl]-(1H,3H,5H)-(1)-benzopyrano-(2,3-d)-pyrimidine-4-one-2-thione in each milliliter is prepared from the following ingredients:

| | |
|---|---|
| 7-[5′tetrazolylaminocarbonyl]-(1H,3H,5H)-(1)-benzopyrano-(2,3-d)-pyrimidine-4-one-2-thione | 5 gm. |
| Benzyl benzoate | 200 ml. |
| Methylparaben | 1.5 gm. |
| Propylparaben | 0.5 gm. |
| Cottonseed oil q.s. | 1000 ml. |

One milliliter of this sterile preparation is injected for prophylactic treatment of allergic rhinitis.

EXAMPLE XV

A powder mixture consisting of 0.1 g. of 7-[5′-tetrazolylaminocarbonyl]-(1H,3H,5H)-(1)-benzopyrano-(2,3-d)-pyrimidine-4-one-2-thione and sufficient lactose to make 5 g. of mixture is micropulverized and placed in an insufflator designed to deliver 50 mg. of powder per dose.

EXAMPLE XVI

Twelve grams of an aerosol composition are prepared from the following ingredients:

| | |
|---|---|
| 7-[5′tetrazolylaminocarbonyl]-(1H,3H,5H)-(1)-benzopyrano-(2,3-d)-pyrimidine-4-one-2-thione | 0.012 gm. |
| Freon 12 | 1.440 gm. |
| Freon 114 | 2.160 gm. |
| Water | 7.788 gm. |
| Sorbitan monoleate | 0.600 gm. |

The compound is dispersed in the water and chilled to −30° C. and added to the chilled Freons. The twelve grams of compositions are added to a 13 ml. plastic coated bottle and capped with a metering valve. The metering valve releases 80 mg. of composition in an aerosol. The aerosol is inhaled every 4 to 6 hours for prevention of asthmatic attacks.

EXAMPLE VXII

The following formulation is suitable for spraying of 0.1 ml. per burst of spray from a squeeze bottle.

| | |
|---|---|
| 7-[5′-tetrazolylaminocarbonyl]-(1H,3H,5H)-(1)-benzopyrano-(2,3-d)-pyrimidine-4-one-2-thione NMG* | 10 mgm/ml. |
| Benzyl alcohol | 10 mgm/ml. |
| Sorbitol, U.S.P. | 40 mgm/ml. |
| Water q.s. | 1 ml. |

*(calculated on the acid)

As is true in any large class of compounds, it is found that certain sub-groups and certain specific compounds are preferred for the therapeutic utility herein described. In general, it is found that the benzenoid substituent ("R", as defined) ought to be located at the 7- and/or 8-positions, preferably the 7-, that "R" represent carboxamido, or loweralkoxycarbonyl, and that (n) is one. The specifically preferred individual compound is 7-[5′-tetrazolylaminocarbonyl]-(1H,3H,5H)-(1)-benzopyrano(2,3-d)-4-one-2-thione, said compound also being preferably administered as its bis-N-methyl-D-glucamine salt, although other preferred compounds are:

7-(n-propyloxycarbonyl)-(1H,3H,5H)-(1)-benzopyrano-(2,3-d)-4-one-2-thione,
7-(n-butyloxycarbonyl)-(1H,3H,5H)-(1)-benzopyrano-(2,3-d)-4-one-2-thione,
7-(isobutyloxycarbonyl)-(1H,3H,5H)-(1)-benzopyrano-(2,3d)-4-one-2-thione,
7-(n-propylaminocarbonyl)-(1H,3H,5H)-(1)-benzopyrano-(2,3-d)-4-one-2-thione,
7-(iso-propylaminocarbonyl)-(1H,3H,5H)-(1)-benzopyrano-(2,3-d)-4-one-2-thione,
7-(iso-butylaminocarbonyl)-(1H,3H,5H)-(1)-benzopyrano-(2,3-d)-4-one-2-thione,
7-(2-(2-pyridyl)-ethylaminocarbonyl)-(1H,3H,5H)-(1)-benzopyrano-(2,3-d)-4-one-2-thione,
7-(2-hydroxy-2-phenylethylaminocarbonyl)-(1H,3H,5H)-(1)-benzopyrano-(2,3-d)-4-one-2-thione.

I claim:

1. A compound of the formula

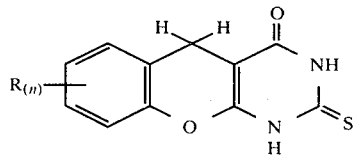

and the pharmaceutically acceptable salts thereof, wherein R represents hydrogen, lower alkyl, lower cyclo alkyl, acyloxylower alkyl, hdyroxylower alkyl, lower alkoxyloweralkyl, nitro, halogeno, hydroxy, lower alkoxy, carboxyl, carboxamido, lower alkoxycarbonyl, tetrazolyl or cyano, and n is one or two, wherein said carboxamido has the partial structural formula

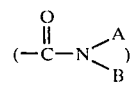

wherein A is straight or branched chain alkyl with up to 12 carbon atoms, lowercycloalkyl, lowercycloalkylloweralkyl, loweralkoxyloweralkyl, hydroxyloweralkyl, fluoroloweralkyl, loweralkenyl, loweralkylthioloweralkyl, loweralkylsulfoxyloweralkyl, loweralkylsulfonylloweralkyl, thiazolyl, oxazolyl, thiadiazolyl, methylthiadizaolyl, furyl, pyrazolyl, tetrazolyl, methyltetrazolyl, phenyl, or the grouping $ER_4$ wherein E is a straight or branched chain or cyclic loweralkylene optionally substituted with hydroxy or phenyl radicals, $R_4$ is phenyl, thiazolyl, oxazolyl, thiadiazolyl, methylthiadiazolyl, tetrazolyl, methyltetrazolyl, furyl, pyridyl, methylpyridyl or piperidinyl; and B is hydrogen, loweralkyl, lowercycloalkyl, lowercycloalkylloweralkyl, or loweralkenyl; or A and B, when taken together with the nitrogen atom to which they are attached, represent imidazolyl, morpholinyl, pyrrolidinyl, piperidinyl or piperazinyl, said heterocyclic rings being optionally substituted by hydroxy, loweralkyl or hydroxyloweralkyl.

2. A compound of claim 1 wherein n is one.

3. A compound of claim 2 wherein R is carboxyl.

4. A compound of claim 2 wherein R is carboxamido.

5. A compound of claim 1 wherein said carboxamido is 5-tetrazolylaminocarbonyl.

6. A compound of claim 5, said compound being 7-[5'-tetrazolylaminocarbonyl]-(1H,3H,5H)-(1)-benzopyrano-(2,3-d)-pyrimidine-4-one-2-thione.

7. A compound of claim 5, said compound being 7-[5'-tetrazolylaminocarbonyl]-(1H,3H,5H)-(1)-benzopyrano-(2,3-d)-pyrimidine-4-one-2-thione-bis-N-methyl-D-glucamine.

8. A compound of claim 1 wherein said carboxamido is imidazolylcarbonyl.

9. A compound of claim 1 wherein said carboxamido is 2-[2-pyridyl] ethylaminocarbonyl.

10. A method for effecting an anti-allergic reaction useful in the prophylactic treatment of animals for allergic and anaphylactic reactions which comprises administering to an animal in need of such therapy a therapeutically useful quantity of a compound of claim 1.

11. An anti-allergy pharmaceutical composition comprising an effective amount of a compound of claim 1 and a pharmaceutically acceptable carrier.

12. A composition according to claim 11 adapted for contact with nasal linings.

13. A nebulizer or spray device containing an effective amount of an aqueous solution of a soluble salt of a compound of claim 1.

* * * * *